US008932563B2

(12) United States Patent
Martinetti et al.

(10) Patent No.: US 8,932,563 B2
(45) Date of Patent: *Jan. 13, 2015

(54) HIGHER LOADING ZINC-CONTAINING FILMS

(75) Inventors: Melissa Martinetti, Bridgewater, NJ (US); Thomas Boyd, Metuchen, NJ (US); James R. Brown, Edison, NJ (US); Betty Won, New Brunswick, NJ (US); Shira Pilch, Highland Park, NJ (US); James Gerard Masters, Ringoes, NJ (US); Paloma Pimenta, Staten Island, NY (US)

(73) Assignee: Colgate-Palmolive Company, New York, NY (US)

( * ) Notice: Subject to any disclaimer, the term of this patent is extended or adjusted under 35 U.S.C. 154(b) by 6 days.

This patent is subject to a terminal disclaimer.

(21) Appl. No.: 13/266,942

(22) PCT Filed: May 26, 2010

(86) PCT No.: PCT/US2010/036143
§ 371 (c)(1),
(2), (4) Date: Oct. 28, 2011

(87) PCT Pub. No.: WO2010/138547
PCT Pub. Date: Dec. 2, 2010

(65) Prior Publication Data
US 2012/0045495 A1 Feb. 23, 2012

Related U.S. Application Data

(60) Provisional application No. 61/181,124, filed on May 26, 2009.

(51) Int. Cl.
| A61K 33/30 | (2006.01) |
| A61K 8/27 | (2006.01) |
| A61Q 11/00 | (2006.01) |
| A61K 8/02 | (2006.01) |
| A61K 8/23 | (2006.01) |
| A61K 8/24 | (2006.01) |
| A61K 8/365 | (2006.01) |

(52) U.S. Cl.
CPC . *A61Q 11/00* (2013.01); *A61K 8/02* (2013.01); *A61K 8/23* (2013.01); *A61K 8/24* (2013.01); *A61K 8/27* (2013.01); *A61K 8/365* (2013.01); *A61K 8/0216* (2013.01)
USPC ............................. 424/49; 424/401; 514/781

(58) Field of Classification Search
USPC .................... 424/401, 49; 514/781
See application file for complete search history.

(56) References Cited

U.S. PATENT DOCUMENTS

| 4,022,880 | A | 5/1977 | Vinson et al. |
| 4,138,477 | A | 2/1979 | Gaffar |
| 4,820,506 | A | 4/1989 | Kleinberg et al. |
| 4,839,157 | A | 6/1989 | Mei-King Ng et al. |
| 4,900,552 | A | 2/1990 | Sanvordeker et al. |
| 5,047,244 | A | 9/1991 | Sanvordeker et al. |
| 5,629,003 | A * | 5/1997 | Horstmann et al. .......... 424/401 |
| 5,695,746 | A | 12/1997 | Garlick, Jr. et al. |
| 5,700,478 | A | 12/1997 | Biegajski et al. |
| 5,948,430 | A | 9/1999 | Zerbe et al. |
| 6,123,965 | A | 9/2000 | Jacob et al. |
| 6,241,974 | B1 | 6/2001 | White, Jr. et al. |
| 6,287,541 | B1 | 9/2001 | Creeth et al. |
| 6,315,986 | B1 | 11/2001 | Wong et al. |
| 6,596,298 | B2 | 7/2003 | Leung et al. |
| 6,669,929 | B1 | 12/2003 | Boyd et al. |
| 2003/0053962 | A1 | 3/2003 | Zerbe et al. |
| 2003/0054034 | A1 | 3/2003 | Leung et al. |
| 2004/0126332 | A1 | 7/2004 | Boyd et al. |
| 2005/0019273 | A1 | 1/2005 | Boyd et al. |
| 2005/0106112 | A1 * | 5/2005 | Boyd et al. ...................... 424/49 |
| 2005/0208110 | A1 * | 9/2005 | Singh et al. ................... 424/443 |
| 2007/0020201 | A1 * | 1/2007 | Boyd et al. ...................... 424/52 |
| 2007/0183989 | A1 * | 8/2007 | Prencipe et al. ................. 424/53 |
| 2008/0138298 | A1 | 6/2008 | Glandorf et al. |
| 2008/0138369 | A1 | 6/2008 | Boyd et al. |

FOREIGN PATENT DOCUMENTS

| JP | 2004-529657 | 9/2004 |
| WO | WO 01/34108 | 5/2001 |
| WO | WO 03/015749 | 2/2003 |
| WO | WO 2004/060335 | 7/2004 |
| WO | WO 2007/013937 | 2/2007 |
| WO | WO 2007/076466 | 7/2007 |
| WO | WO 2008/008617 | 1/2008 |
| WO | WO 2008/041055 | 4/2008 |
| WO | WO 2008/130764 | 10/2008 |
| WO | WO 2010/114546 | 10/2010 |

OTHER PUBLICATIONS

Gan et al., 2009, "Antibacterial Activity of Zinc-Chelator Complexes," The Preliminary Program for IADR/AADR/CADR 87th General Session and Exhibition (Apr. 1-4, 2009).

(Continued)

Primary Examiner — Lezah Roberts
(74) Attorney, Agent, or Firm — Howard C. Lee

(57) ABSTRACT

Described herein are polymer matrix films, compositions comprising the polymer matrix films, and methods of preparing and using the same.

13 Claims, 2 Drawing Sheets

(56) References Cited

OTHER PUBLICATIONS

Hider et al., 1990, "Facilitated uptake of zinc into human erythrocytes. Relevance to the treatment of sickle-cell anaemia," Biochem. Pharmacol, 39(6):1005-1012.
International Search Report and Written Opinion in international Application No. PCT/U10/036041, mailed Mar. 28, 2011.
International Search Report and Written Opinion in International Application No. PCT/US10/036140, mailed Mar. 25, 2011.
International Search Report and Written Opinion in International Application No. PCT/US10/036143, mailed Mar. 25, 2011.
Majitihya et al., 2008, "Mucoadhesion Enhancement: Enhancement of Mucoadhesion by Blending Anionic, Cationic & Nonionic Polymers," Drug Delivery Tech. 8:40-45.
Muller et al., 1996, "The Effect of pH on the Corrosion Inhibition of Zinc Pigments by Phenol Derivatives," Corrosion Science 38(11):1869-1875.
Vasir et al., 2003, "Bioadhesive microspheres as a controlled drug delivery system," Int J. Pharmaceutics 255(1-2):13-32.

* cited by examiner

HIGHER LOADING ZINC-CONTAINING FILMS

CROSS-REFERENCE TO RELATED APPLICATIONS

The present application is a national stage entry under 35 U.S.C. §371 of International Patent Application No. PCT/US2010/036143, filed May 26, 2010, which claims priority to U.S. Provisional Patent Application Ser. No. 61/181,124, filed on May 26, 2009, the entireties of which are hereby incorporated by reference.

BACKGROUND

This application relates to oral and personal care compositions, and more particularly to compositions comprising a film entrained in a carrier, in which the film includes a relatively high concentration of zinc-containing compound. Such compositions include, for example, dentifrices.

The aesthetic appeal of such compositions is important, and can have significant effects on consumer acceptance and usage. Aesthetic effects have been acknowledged to play an important role in consumer acceptance of many products. Although such products have met with consumer approval, the art seeks to further improve the aesthetic effects as well as the cosmetic and therapeutic benefits of these products. Indeed, many such compositions known in the art are deficient in one or more attributes.

Compositions for enhancing health, hygiene or appearance, such as oral care compositions, skin care compositions and hair care compositions, are used by millions of people. These compositions are used for a wide variety of purposes, including for enhancing personal health, hygiene, and appearance, as well as for preventing or treating a variety of diseases and other conditions in humans and in animals.

The formulation of such compositions presents a number of challenges. They must be pharmaceutically and/or cosmetically acceptable for their intended use. Compositions that contain therapeutic active materials preferably deliver the active at effective levels, avoiding undue chemical degradation. Similarly, compositions containing cosmetically functional materials must deliver the material to, e.g., the oral cavity, skin or hair at effective levels under the conditions that they are typically used by the consumer.

Water-soluble films for oral administration of therapeutic agents are well known in the art. It is also known in the no to use such films for administering a breath freshening agent, e.g., menthol. The known films for administering breath freshening agents and/or active pharmaceutical agents are generally comprised of at least one water-soluble polymer suitable for human consumption and at least one compound that enhances the wettability of the water-soluble polymer, typically selected from polyalcohols, surfactants and plasticizers. For example, U.S. Pat. No. 5,948,430, the disclosure of which is incorporated by reference herein in its entirety, describes a monolayer film that can be adhered to the oral cavity to release a pharmaceutically or cosmetically active ingredient, wherein the film comprises at least one water-soluble polymer; at least one member selected from the group consisting of a polyalcohol, a surfactant and a plasticizer; at least one cosmetic or pharmaceutically active ingredient; and a flavoring agent.

U.S. Pat. No. 5,700,478, the disclosure of which is incorporated by reference herein in its entirety, describes a laminated device for controlled release of a substance within a mucosa-lined body cavity including a water-soluble adhesive layer comprised of a water-soluble polymer and a water-soluble plasticizer, and a water-soluble polymer layer. This patent teaches a multiple layer laminate that dissolves relatively slowly for controlled or sustained release of a substance.

U.S. Pat. No. 4,900,552, the disclosure of which is incorporated by reference herein in its entirety, describes a trilaminate film suitable for prolonged and sustained delivery of an active ingredient in a buccal cavity. The trilaminate includes a hydratable muco-adhesive base layer; a non-adhesive reservoir layer; and a water-impermeable barrier sandwiched between and bonded to the base layer and the reservoir layer. This patent discloses slowly disintegrating films for prolonged or sustained release of a substance.

U.S. Pat. No. 5,047,244, the disclosure of which is incorporated by reference herein in its entirety, discloses a therapeutic dosage form comprising an anhydrous but hydratable monolithic polymer matrix that contains amorphous fumed silica as well as a therapeutic agent, and a water-insoluble barrier layer secured to the polymer matrix and defining a non-adhesive face. This patent does not disclose rapidly disintegrating films, but instead contemplates compositions that are capable of providing improved availability of therapeutic agents from a controlled release muco-adhesive carrier system.

U.S. Pat. No. 6,669,929, and U.S. Patent Application Publication No. 2003/0053962, the disclosures of each of which are incorporated by reference herein in their entirety, disclose film forming agents useful in oral care compositions. The films dissolve in the mouth and release functional components, typically flavorants.

It is known to incorporate flavorants, colorants, and some active components in films that dissolve in the oral cavity. These films are used either by themselves as breath freshening strips, teeth whitening strips, or as polymer flakes dispersed throughout an oral care composition. It also is known to incorporate zinc salts in dentifrice formulations. Use of various zinc salts often is limited by the solubility of the zinc, undesirable consumer astringency when higher levels of zinc are utilized, and the reactivity of the zinc once zinc ions that are available for reaction (i.e., the zinc ions sometimes cause adverse reactions within the formulation).

Thus, there is an ongoing need for new oral and personal care compositions, and methods of their use.

SUMMARY

The present invention provides, in various embodiments, oral and personal care compositions comprising a film entrained in a carrier, in which the film includes a relatively high concentration of a zinc-containing compound. In one embodiment, the film is provided as a plurality of film fragments. In various embodiments, the present invention provides compositions comprising a plurality of lamellar fragments in a carrier.

In one embodiment, the oral care composition comprises a film entrained in a carrier, in which a zinc-containing compound is contained in the film in an amount from about 35% by weight to about 60% by weight. Increasing the solid loading in the film formula increases the delivery of actives per area which is important for delivering superior efficacy.

The embodiments also provide methods for making the film and methods for administering a zinc-containing compound to a human or animal subject in need thereof, the method including topically applying to the subject an oral care composition comprising a film entrained in a carrier, a zinc-containing compound contained in the film, a polysaccharide, and a maleic anhydride copolymer. In various methods, such methods further comprise disrupting the film after the topical application.

Compositions and methods of this invention afford benefits over compositions and methods among those known in the art. Such benefits include one or more of increased consumer acceptability, improved amounts of available zinc, decreased adverse reactions brought about by the presence of zinc ions, enhanced aesthetics, improved stability for active or other functional materials, and controlled delivery of active materials such as zinc. Further benefits and embodiments of the present invention are apparent from the description set forth herein.

BRIEF DESCRIPTION OF THE DRAWINGS

Preferred embodiments of the invention are described in the examples that follow, and illustrated in some of the figures appended hereto, in which.

DETAILED DESCRIPTION

Figure 1:
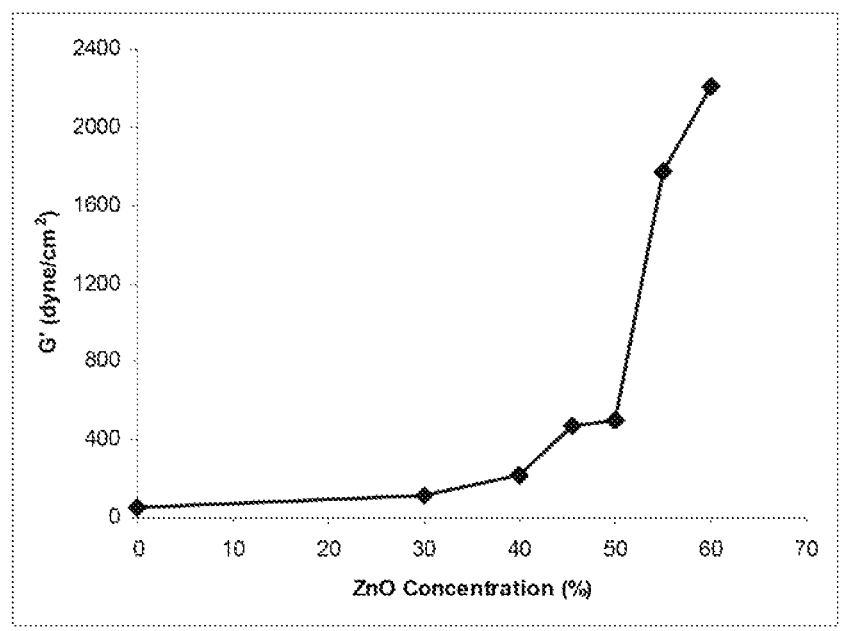
FIG. 1 shows the effect of the elastic modulus (G') of the film slurries as a function of zinc oxide concentration, as prepared in accordance with Example 2.

The present invention provides compositions and methods for administration to, or use with, a human or other animal subject. Preferably, specific materials and compositions to be used in this invention are, accordingly, pharmaceutically- or cosmetically-acceptable. As used herein, such a "pharmaceutically acceptable" or "cosmetically acceptable" component is one that is suitable for use with humans and/or animals to provide the desired therapeutic, sensory, decorative, or cosmetic benefit without undue adverse side effects (such as toxicity, astringent taste, irritation, and allergic response) commensurate with a reasonable benefit/risk ratio. The following definitions and non-limiting guidelines must be considered in reading and interpreting the description of this invention set forth herein.

The headings (such as "Introduction" and "Summary,") used herein are intended only for general organization of topics within the disclosure of the invention, and are not intended to limit the disclosure of the invention or any aspect thereof. In particular, subject matter disclosed in the "Introduction" may include aspects of technology within the scope of the invention, and may not constitute a recitation of prior art. Subject matter disclosed in the "Summary" is not an exhaustive or complete disclosure of the entire scope of the invention or any embodiments thereof.

The citation of references herein does not constitute an admission that those references are prior art or have any relevance to the patentability of the invention disclosed herein. All references cited in the Description section of this specification are hereby incorporated by reference in their entirety.

The description and specific examples, while indicating embodiments of the invention, are intended for purposes of illustration only and are not intended to limit the scope of the invention. Recitation of multiple embodiments having stated features is not intended to exclude other embodiments having additional features, or other embodiments incorporating different combinations of the stated features. Specific Examples are provided for illustrative purposes of how to make, use and practice the compositions and methods of this invention and, unless explicitly stated to recite activities that have been done (i.e., using the past tense), are not intended to be a representation that given embodiments of this invention have, or have not, been performed.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention. As used herein, the word "include," and its variants, is intended to be non-limiting, such that recitation of items in a list is not to the exclusion of other like items that may also be useful in the materials, compositions, devices, and methods of this invention. In a similar manner, the description of certain advantages or disadvantages of known materials and methods is not intended to limit the scope of the embodiments to their exclusion. Indeed, certain embodiments may include one or more known materials or methods, without suffering from the disadvantages discussed herein.

As used herein, the term "comprising" means that other steps and other components that do not affect the end result may be utilized. The term "comprising" encompasses the expressions "consisting of," and "consisting essentially of." The expression "effective amount," as used herein denotes an amount of a compound or composition sufficient to significantly induce a positive benefit, preferably an oral health benefit, but low enough to avoid serious side effects, i.e., to provide a reasonable benefit to risk ratio, within the sound judgment of a person having ordinary skill in the art. The use of singular identifiers such as "the," "a," or "an" is not intended to be limiting solely to the use of a single component, but may include multiple components.

The oral care compositions of the various embodiments preferably are in the form of a dentifrice. The term "dentifrice" as used throughout this description, denotes a paste, gel, or liquid formulation. The dentifrice may be in any desired form, such as deep striped, surface striped, multi-layered, having a gel surround the paste, or any combinations thereof. The film contained in the oral care composition may be of any desired shape or structure, including multiple small strips, or one continuous strip.

The expressions "carrier" or "aqueous carrier" as used throughout this description denote any safe and effective materials for use herein. Such materials include, for example, thickening agents, humectants, ionic active ingredients, buffering agents, anticalculus agents, abrasive polishing materials, peroxide sources, alkali metal bicarbonate salts, surfactants, titanium dioxide, coloring agents, flavor systems, sweetening agents, antimicrobial agents, herbal agents, desensitizing agents, stain reducing agents, and mixtures thereof.

All percentages and ratios used herein are by weight of the oral care composition, unless otherwise specified. All measurements are made at 25° C., unless otherwise specified.

The present invention provides oral or personal care compositions comprising a film entrained in a carrier, wherein the film comprises a relatively high concentration of a zinc-containing compound. As referred to herein, an "oral or personal care composition" is any composition that is suitable for administration or application to a human or animal subject for enhancing the health, hygiene or appearance of the subject, including the prevention or treatment of any physiologic condition or disorder, and providing sensory, decorative or cosmetic benefits and combinations thereof. Compositions among those provided herein include oral care compositions, skin care compositions, hair care composition, topical pharmaceutical compositions, and ocular compositions. By "oral care composition" as used herein is meant a composition for which the intended use can include oral care, oral hygiene, or oral appearance, or for which the intended method of use can comprise administration to the oral cavity.

Embodiments of this invention comprise a film. As referred to herein, a "film" is a material having a substantially lamellar structure. A "lamellar" structure has, or is capable of having, a size in one or two dimensions (e.g., the x- or y-dimensions) that is substantially greater than the thickness of the structure in a third dimension (e.g., the z-direction). Lamellar structures among those useful herein include those that are substantially planar, layered, or lamelliform. In one embodiment, the lamellar structure is substantially planar, having a size in both the x- and y-dimensions that is substantially greater than the z-direction. In other embodiments, the lamellar structure is non-planar. In one embodiment, a film of this intention comprises a substantially continuous surface that can appear as a substantially flat surface, although in some embodiments the film is deformed. In such embodiments, the film can have any of a number of shapes, including having a smooth curved surface.

Films among those useful herein may be rigid or plastic, comprising any of a variety of materials, including materials selected from the group consisting of film forming materials, clays, waxes, and mixtures thereof. In one embodiment, the film comprises a film forming polymer. Film forming polymers among those useful herein include materials selected from the group consisting of water soluble polymers, water dispersible polymers, water insoluble polymers, and mixtures thereof.

In some embodiments, a film comprises at least one film forming material. In certain embodiments, a film forming material is a polymer. Polymers useful herein include hydrophilic polymers and hydrophobic polymers. In certain embodiments, the polymer is a water soluble polymer. In some embodiments, the polymer is a water soluble, breakable polymer that dissolves during use, such as, for example, during toothbrushing. The dissolution can occur as a result of, for example, shearing and/or exposure to a solvent comprising a high concentration of water, such as saliva. In some embodiments, the polymer is insoluble but breakable in water by being dispersible, i.e., the polymer breaks down into small fragments, for example, as a result of shearing. In some embodiments, a polymer is insoluble but swellable. In configurations in which a polymer does not break down during use, the polymer can be a water-repellant polymer or an aqueous-stable hydrophilic polymer such as certain types of cellulose, for example paper. In some embodiments, a film fragment can comprise a mixture of film forming materials.

Water soluble polymers among those useful herein include cellulose ethers, methacrylates, polyvinylpyrollidone, and mixtures thereof. In one embodiment, the polymer is a cellulose ether, including those selected from the group consisting of hydroxyalkyl cellulose polymers such as hydroxypropyl methyl cellulose (HPMC), hydroxypropyl cellulose, hydroxyethyl cellulose, methyl cellulose, carboxymethyl cellulose, and mixtures thereof. Other polymers among those useful herein include polyvinylpyrrolidone, cross-linked polyvinyl pyrrolidone, polyvinylpyrrolidone-vinyl acetate copolymer, polyvinylalcohol, polyacrylic acid, poly acrylate polymer, cross-linked polyacrylate polymer, cross-linked polyacrylic acid (e.g, Carbopol®), polyethylene oxide, polyethylene glycol, poly vinylalkyl ether-maleic acid copolymer (such as Gantrez®) and carboxy vinyl polymer; natural gums such as sodium alginate, carrageenan, xantham gum, gum acacia, arabic gum, guar gum, pullulan, agar, chitin, chitosan, pectin, karaya gum, zein, hordein, gliadin, locust bean gum, tragacantha and other polysaccharides; starches such as maltodextrin, amylose, high amylose starch, corn starch, potato starch, rice starch, tapioca starch, pea starch, sweet potato starch, barley starch, wheat starch, waxy corn starch, modified starch (e.g. hydroxypropylated high amylose starch), dextrin, levan, elsinan and gluten; and proteins such as collagen, whey protein isolate, casein, milk protein, soy protein and gelatin.

Non-limiting examples of water dispersable and swellable polymers include modified starch, alginate esters, divalent or multivalent ion salts of alginates. Non-limiting examples of water insoluble polymers include polymers soluble in at least one organic solvent, such as cellulose acetate, cellulose nitrate, ethylene-vinyl acetate copolymers, vinyl acetate homopolymer, ethyl cellulose, butyl cellulose, isopropyl cellulose, shellac, silicone polymer (e.g. dimethylsilicone), PMMA (poly methyl methacrylate), cellulose acetate phthalate and natural or synthetic rubber; polymers insoluble in organic solvents, such as cellulose, polyethylene, polypropylene, polyesters, polyurethane and nylon.

The films useful in the various embodiments can be made in accordance with the methods described in U.S. Pat. No. 6,669,929, and U.S. Patent Application Publication No. 2003/0053962, the disclosures of which are incorporated by reference herein in their entirety. The zinc-containing compounds contained within the film can be incorporated into the film during film manufacture using techniques known in the art. A person having ordinary skill in the art will be capable of making the film containing the zinc-containing compound, using the guidelines provided herein.

The polymer matrix used in many dissolvable films, which are preferred in certain embodiments, has a limited capacity of the amount of solids it can hold. Certain formulation modifications can be performed, however, to increase the integrity of the film matrix to hold high loadings of solids. The preferred polymer matrix used in particularly preferred embodiments includes two different molecular weights of hydroxypropylmethylcellulose (HPMC) specifically, Methocel E5 and E50, commercially available from Dow Chemical, Midland, Mich. Modifying the polymer system can increase the strength of the film matrix to support a high loading of solids, especially zinc oxide. By rebalancing the polymer system, the present inventors discovered a method in which more actives can be loaded into the film than could be done previously. This creates a film with a higher concentration of zinc-containing compound that can be delivered, and also reduces the amount of film needed to deliver these higher amounts. The improved higher loading zinc-containing film formula provides higher deposition onto surfaces for superior efficacy. Also, improving the film formulation to hold a higher loading of zinc-containing compound can reduce the amount of total film needed in a product, while at the same time, delivering the same efficacy as with a lower loading of film.

In various embodiments, the oral care compositions comprise a plurality of lamellar film fragments entrained in a carrier. In one embodiment, the composition comprises a film, wherein the film comprises lamellar fragments of the film material. In one embodiment, the composition comprises a carrier having distributed therein a plurality of lamellar fragments, wherein the fragments comprise a matrix and a functional zinc-containing compound material. In one such embodiment, the matrix comprises a film. Such fragments may be of any of a variety of shapes or forms, including semi-solid or solid discrete portions, fragments, particles, flakes, or combinations thereof. In various embodiments, the film comprises a first plurality of fragments and a second plurality of fragments, wherein the first plurality of fragments differ in composition or appearance from the second plurality of fragments. Such difference in composition or appearance can be in any aspect of the composition of the fragment (e.g., different film components, different functional material, different formulation colorant), different appearance (e.g., shape, color, texture, refractive index, reflective index), or combinations thereof.

In various embodiments, the fragments exhibit perceivable contrast with the carrier. The perceivable contrast can be sensory contrast, such as optical contrast, tactile contrast, taste contrast, or olfactory contrast. In some configurations, optical contrast can be color contrast, or a difference in refractive index or reflective index. In some configurations, color contrast can be imparted by one or more colorants that comprise different components of the composition. In various embodiments, the present invention provides compositions comprising a plurality of film fragments in a carrier, wherein said fragments are visibly discernable. As referred to herein, "visibly discernable" refers to one or more characteristics of a fragment which cause the fragment to have a different physical appearance, preferably to the naked eye, relative to the carrier in which the fragment is entrained. Such characteristics include color, opacity, refractive index, reflective index, size, shape, and combinations thereof.

In various embodiments, the fragments have a non-random shape. In one embodiment, a "non-random" shape is a shape which results from a manufacturing process of shaping, cutting, or other forming process by which a specific shape is imparted to a fragment. In such embodiments, a non-random shape is distinguished from such shapes that result from simple precipitation or grinding of a material. In one embodiment, a "non-random" shape is "repeating," wherein the composition comprises a plurality of fragments have substantially the same shape. Such repeating shape may have any of a variety of forms, and may be selected based on a variety of aesthetic or functional criteria. In certain embodiments, the shape of a film fragment can be a recognizable shape. In certain embodiments, a film fragment can comprise a nonrandom shape. Such shapes include simple geometric shapes, such as polygons and elliptical shapes, such as triangles, quadrilaterals (such as a square, a rectangle, a rhombus), pentagons, hexagons, oval, and circles. In one embodiment, the repeating shape is a square. Repeating shapes include, in other embodiments, shapes that are representative of figures or animate or inanimate objects, such as stars, hearts, gems, flowers, trees, shamrocks, a letter of an alphabet, numbers, animals, people, and faces. In various embodiments, the composition comprises a single repeating shape. In other embodiments, the composition comprises a plurality of fragments having a plurality of repeating shapes. In one embodiment, the compositions of the present invention comprise a plurality of first film fragments having a first repeated shape and a plurality of second film fragments having a second repeated shape, wherein the first repeated shape is different from the second repeated shape.

In various embodiments, the size of the fragments is not critical, and may be determined pursuant to any of a variety of criteria, including manufacturing convenience, affect on visual appearance, surface area, affect on texture in the composition, and combinations thereof. In some embodiments, the film fragments can be up to about 1 inch (25.4 mm) in length in the longest dimension. As referred to herein, "long dimension" is the dimension of a fragment in length or width (i.e., in the x- and y-dimensions, as the fragment is, or is deformed to be, in a planar shape) in a dimension substantially perpendicular to the "thickness" or shortest dimension of the fragment (i.e., the z-dimension). It is understood that in various embodiments comprising a plurality of fragments, the fragments may be present in a range of sizes due to a variety of factors, including random variation in size, manufacturing tolerances, and intentional sizing or mixing of the fragments through sieving or similar means. As referred to herein, sizes refer to the average size of fragments in a given plurality of fragments.

In various embodiments, the fragments are from about 0.2 mm to about 15 mm in long dimension. In various embodiments, the long dimension of the fragments is from 0.2 mm to about 10 mm, from about 0.5 mm to about 10 mm, from about 0.8 mm to about 8 mm, from about 0.9 mm to about 5 mm, from about 1.0 mm to about 5 mm, or from about 1.5 mm to about 2.5 mm. In some embodiments, the long dimension of the fragments is at least about 3 mm, and can be from about 6 mm to about 13 mm. In certain embodiments, a plurality of film fragments are greater than about 600 microns in the longest dimension. In certain embodiments, a plurality of film fragments are greater than about 1 millimeter in the longest dimension.

In various embodiments, the fragments of the present invention have a thickness of from about 1 mil (thousandth of an inch, 25.4 microns) to about 3 mils (76.2 microns). In various embodiments, the fragments have a thickness of less than about 4 mils or less than about 100 microns and from about 0.1 mils (2.54 microns) up to about 10 mils (254 microns), from about 0.5 mils (12.7 microns) up to about 5 mils (127 microns), from about 1.4 mils (35.6 microns) to about 2.0 mils (50.8 microns).

In some embodiments, the compositions of the present invention comprise fragments having an aspect ratio of at least about 5:1. As referred to herein, "aspect ratio" of a fragment is the ratio of the diameter of the smallest imaginary sphere that can enclose the object to the diameter of the largest imaginary sphere that can be completely inside the object and tangent to the surfaces of the object. For example, the aspect ratio of a sphere is 1:1; in another example, the aspect ratio of a cylinder that is 2 inches (50.8 mm) long and ¼ inch (6.35 mm) in diameter is slightly over 8:1; in yet another example, a film fragment of the present invention that is 1 mil (25.4 microns) in thickness, 1 inch (25.4 mm) in length, and 1 inch (25.4 mm) wide has an aspect ratio of about 1414:1.

In some embodiments, the compositions of the present invention comprise fragments having an aspect ratio of at least about 10:1. In various embodiments, the fragments have an aspect ratio of from about 5:1 to about 10,000:1, from about 5:1 to about 500:1, from about 10:1 to about 1,000:1, from about 10:1 to about 100:1, from about 20:1 to about 100:1, or from about 25:1 to about 35:1.

In various embodiments, the film comprises a formulation colorant that imparts a color to the film, the composition, or both. In various embodiments, the film fragments contrast with the carrier, and are white, black, or of any color that is visible against or contrasts with the carrier background. Formulation colorants among those useful herein include non-toxic water soluble dyes or pigment, such as, for example, metallic oxide "lakes." In certain embodiments, the colorant is approved for incorporation into a food or drug by a regulatory agency, such as FD&C or D&C pigments and dyes approved by the FDA for use in the United States. Colorants among those useful herein include FD&C Red No. 3 (sodium salt of tetraiodofluorescein), Food Red 17, disodium salt of 6-hydroxy-5-{(2-methoxy-5-methyl-4-sulphophenyl)azo}-

2-naphthalenesulfonic acid, Food Yellow 13, sodium salt of a mixture of the mono and disulphonic acids of quinophtalone or 2-(2-quinolyl)indanedione, FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)-Δ-3,5-cyclohexadienimine], FD&C Blue No. 1 (disodium salt of dibenzyldiethyldiaminotriphenylcarbinol trisulfonic acid anhydrite), FD&C Blue No. 2 (sodium salt of disulfonic acid of indigotin), and mixtures thereof in various proportions. In one embodiment, the colorant comprises a water insoluble inorganic pigment, such as titanium dioxide, chromium oxide green, phthalocyanine green, ultramarine blue, ferric oxide, or a water insoluble dye lake. In some embodiments, dye lakes include calcium or aluminum salts of an FD&C dye such as FD&C Green #1 lake, FD&C Blue #2 lake, D&C Red #30 lake or FD&C # Yellow 15 lake. In certain embodiments, a water soluble dye, such as, for example, FD&C Blue #1, is contained within a water-insoluble polymer such as, for example polyethylene such as that found in polyethylene beads (e.g., Microblue Spectrabeads, sold by Micropowders, Inc.). In certain embodiments, the film comprises a dye such as D&C Red #30. In certain embodiments, a white colorant is used, for example titanium dioxide ($TiO_2$), titanium dioxide coated mica (e.g., Timiron), a mineral, or a clay. In certain embodiments, the colorant is a non-bleeding dye. In various embodiments, the film comprises a colorant at a level of from about from 0.5% to about 20% by weight of the film, or from about 1% to about 15% by weight of the film, or from about 3% to about 12% by weight of the film. In one embodiment, the compositions of the present invention comprise a first plurality of film fragments comprising a first color, and a second plurality of film fragments comprising a second color. Preferably, the second color is different than the first color.

The film of the present invention, in various embodiments, disintegrates during use of the composition. In other embodiments, the film does not disintegrate during use of the composition. In some embodiments, the film releases a material, such as the zinc-containing compound, into the carrier. As referred to herein, "disintegrate" refers to physical disruption of the film or fragment material, so as to produce a film or film fragments of reduced size compared to the original film. Such disruption may be through mechanical, chemical, or physical-chemical means. The disintegration can result, for example, from shearing, grinding, or exposure to elevated temperatures during use. In various dentifrice embodiments of the present invention, such disintegration results from brushing of the composition on the teeth of the subject using the composition. In one embodiment, the film disintegrates so as to release the zinc-containing compound, and consequently, release zinc ions. In some embodiments, a film fragment can disintegrate into small pieces that are not visually discernable. In some embodiments, the film fragments disintegrate to collectively form a colloid or gel.

In various embodiments, the film may comprise, in addition to the zinc-containing compound other therapeutic actives. As referred to herein, a therapeutic active is a material that is useful for the prevention or treatment of a physiological disorder or condition. Such disorders or conditions include those of the oral cavity (including the teeth and gingiva), skin, hair, and eyes. The specific therapeutic active is preferably determined according to the desired utility of the composition. Such actives include the following.

A. antimicrobial agents, such as triclosan, cetyl pyridium chloride, domiphen bromide, quaternary ammonium salts, sanguinarine, fluorides, alexidine, octonidine, EDTA, essential oils such as thymol, methyl salicylate, eucalyptol and menthol, and the like,
B. non-steroidal anti-inflammatory drugs, such as aspirin, acetaminophen, ibuprofen, ketoprofen, diflunisal, fenoprofen calcium, naproxen, tolmetin sodium, indomethacin, and the like,
C. anti-tussives, such as benzonatate, caramiphen edisylate, menthol, dextromethorphan hydrobromide, chlophedianol hydrochloride, and the like,
D. decongestants, such as pseudoephedrine hydrochloride, phenylepherine, phenylpropanolamine, pseudoephedrine sulfate, and the like,
E. anti-histamines, such as brompheniramine maleate, chlorpheniramine maleate, carbinoxamine maleate, clemastine fumarate, dexchlorpheniramine maleate, diphenhydramine hydrochloride, diphenylpyraline hydrochloride, azatadine meleate, diphenhydramine citrate, doxylamine succinate, promethazine hydrochloride, pyrilamine maleate, tripelennamine citrate, triprolidine hydrochloride, acrivastine, loratadine, brompheniramine, dexbrompheniramine, and the like,
F. expectorants, such as guaifenesin, ipecac, potassium iodide, terpin hydrate, and the like,
G. anti-diarrheals, such a loperamide, and the like,
H. $H_2$-antagonists, such as famotidine, ranitidine, and the like; and
I. proton pump inhibitors, such as omeprazole, lansoprazole, and the like,
J. general nonselective CNS depressants, such as aliphatic alcohols, barbiturates and the like,
K. general nonselective CNS stimulants such as caffeine, nicotine, strychnine, picrotoxin, pentylenetetrazol and the like,
L. drugs that selectively modify CNS function such as phenyhydantoin, phenobarbital, primidone, carbamazepine, ethosuximide, methsuximide, phensuximide, trimethadione, diazepam, benzodiazepines, phenacemide, pheneturide, acetazolamide, sulthiame, bromide, and the like,
M. antiparkinsonism drugs such as levodopa, amantadine and the like,
N. narcotic-analgesics such as morphine, heroin, hydromorphone, metopon, oxymorphone, levorphanol, codeine, hydrocodone, xycodone, nalorphine, naloxone, naltrexone and the like,
O. analgesic-antipyretics such as salycilates, phenylbutazone, indomethacin, phenacetin and the like,
P. psychopharmacological drugs such as chlorpromazine, methotrimeprazine, haloperidol, clozapine, reserpine, imipramine, tranylcypromine, phenelzine, lithium and the like.

The amount of medicament that can be used in the films can be dependent upon the dose needed to provide an effective amount of the medicament. In a particularly preferred embodiment, triclosan is not used, and the primary anti-bacterial agent is the zinc-containing compound.

In various embodiments, therapeutic agents useful herein include anticaries agents, tartar control agents, antiplaque agents, periodontal actives, breath freshening agents, malodour control agents, whitening agents, antibacterials, steroids, anti-inflammatory agents, vitamins, proteins, conditioning agents, moisturizers, antiperspirant actives, deodorant actives, anesthetics, and mixtures thereof.

In certain oral care embodiments, the film or the oral care composition may comprise an oral care active, which is useful for the prevention or treatment of an oral care disorder or condition. Oral care actives among those useful herein include abrasives, anticaries agents, tartar control agents, antiplaque agents, periodontal actives, breath freshening agents, malodour control agents, tooth desensitizers, salivary stimulants, whitening agents, and combinations thereof. Active materials among those useful herein are described in U.S. Pat. No. 6,596,298, Leung et al.

Tartar control agents among those useful herein include dialkali or tetraalkali metal pyrophosphate salts such as $Na_4P_2O_7$, $K_4P_2O_7$, $Na_2K_2P_2O_7$, $Na_2H_2P_2O_7$ and $K_2H_2P_2O_7$; long chain polyphosphates such as sodium hexametaphosphate; and cyclic phosphates such as sodium trimetaphosphate. In some configurations, a polyphosphate is a beta.-phase calcium pyrophosphate, such as disclosed in U.S. Pat. No. 6,241,974 to White, Jr. In some embodiments, the film comprises an anticalculus agent at a level of about 15 to 20% by weight of the film.

Odor reducing agents useful herein include sulfur precipitating agents. Such sulfur-precipitating agents include metal salts, such as a copper salt or a zinc salt. Such salts include copper gluconate, zinc citrate and zinc gluconate. These zinc salts can be used in combination or in addition to the zinc-containing compounds included in the film. In various embodiments, the film comprises sulfur precipitating agents at a level of from about 0.01 to about 30% by weight of film, from about 2% to about 2.5% by weight of film, or about 10% to about 20% by weight of film.

In certain embodiments, the film and/or oral composition may include a saliva stimulating agent (a "succulent"). Such agents include those disclosed in U.S. Pat. No. 4,820,506 to Kleinberg et al. In some configurations, a saliva stimulating agent can include a food acid such as citric, lactic, malic, succinic, ascorbic, adipic, fumaric and tartaric acids. In various embodiments, the film comprises a saliva stimulating agent at a level of from about 0.01 to about 12% by weight of the film, from about 1% to about 10% by weight of the film, or from about 2.5% to about 6% by weight of the film. In some embodiments, a saliva stimulating agent can be used in the amelioration of dry mouth.

In certain oral care embodiments, the film comprises other active materials, such as antibacterial agents such as magnolia extract, triclosan, grapeseed extract, thymol, methyl salicylate, eucalyptol, menthol, hop acids, cetyl pyridinium chloride, (including CPC/Zn and CPC+enzymes) and usnic acid; anti-inflammatory agents such a breath freshening agents (for example zinc gluconate, zinc citrate, zinc chlorite and alpha ionone); tooth desensitizers such as potassium nitrate, desensitizing polymers, and desensitizing minerals; anti-inflammatory agents such as magnolia extract, ursolic acid; aloe, and cranberry extract; vitamins such as pantheon, retinyl palmitate, folic acid, tocopherol acetate and Vitamin A; herbs or herbal extracts such as rosemary, oregano, chamomilla recutita, mentha piperita, salvia officinalis, orcommiphora and myrrha; proteins, such as milk proteins and enzymes such as peroxide-producing enzymes, amylase, plaque-disrupting agents such as papain, glucoamylase, glucose oxidase, and "next generation" enzymes; whitening agents such as hydrogen peroxide, urea peroxide and phosphate salts; medicinals, such as aspirin (acetyl salicylic acid), caffeine, and benzocaine; probiotics; abrasives such as silicas (including high cleaning silica), anti-caries agents such as stannous salts (e.g., stannous fluoride) or amino fluoride; a nitric oxide synthase inhibitor such as guanidinoethyldisulfide; calcium; antiattachment ingredients, such as polyumylphosphonic acid; preservatives such as Solbrol® (Bayer Chemicals AG); silicones; chlorophyll compounds, anti-leukoplakia agents such as beta-carotene; anti-oxidants such as Vitamin E; and combinations thereof. In some embodiments, the films comprise such active materials at a concentration of about 0.01 to about 30% by weight of film, from about 2% to about 25% by weight of the film, or from about 10% to about 20% by weight of film.

In certain embodiments, the film and/or oral care composition includes a preservative. A preservative can be added in amounts from about 0.001 wt % to about 5 wt %, preferably from about 0.01 wt % to about 1 wt % of the film. Non-limiting examples of preservatives include sodium benzoate and potassium sorbate.

In certain embodiments, the entrainment of the zinc-containing compound in the film matrix suspended in the dentifrice or other composition isolates these agents from interaction with reactive ingredients present in the composition so that the agents are maintained substantially separate from the reactive composition ingredients during manufacture and storage while subsequently being released from the film matrix when the composition is used. Isolation not only avoids adverse reactions that may occur between the zinc-containing compound and other components that are present in the carrier material, but also avoids dissolution of the zinc-containing compound and premature release of zinc ions, as well as reducing the astringent taste associated with the use of zinc-containing compounds.

The compositions of the present invention comprise a carrier in which a film, or fragments, is entrained. As referred to herein, a "carrier" is any material or composition in which a film can be entrained and is suitable for administration or application to the human or animal subject to whom the composition is administered or applied. As referred to herein, "entrained" refers to the embedding or suspension of a film in a carrier. In various embodiments comprising a plurality of fragments, such fragments may be entrained by embedding, suspension, dispersion or other distribution of the fragments in the carrier. In various embodiments, the fragments are distributed substantially homogenously throughout the carrier. In other embodiments, the fragments are not distributed homogenously in the carrier. In certain embodiments, the distribution of a plurality of film fragments is substantially isotropic within the carrier. Dentifrice compositions that include a plurality of film fragments dispersed or suspended in a carrier are commercially available under the tradename Max Fresh® or Max White®, from Colgate-Palmolive Company, New York, N.Y.

The film includes a zinc-containing compound that provides a source of zinc ions. Zinc ions have been found to help in the reduction of gingivitis, plaque, sensitivity, and improved breath benefits. Many zinc-containing compounds, however, are sparingly soluble and hence, must be used in relatively large amounts to provide an effective amount of zinc ions. Unfortunately, many zinc-containing compounds also have unpleasant consumer astringency, especially when used in relatively high concentration. The present invention provides a mechanism that increases the amount of available zinc ions, thus permitting the use of lower concentrations of film to achieve the same or more beneficial effect.

The presence of the zinc-containing compound in a film allows for the incorporation of a relatively insoluble compound into a dentifrice. The method of action of films in dentifrice formulations typically is based on the mucoadhesiveness of the film and subsequent retention of the films in the mouth, as the insolubility of the zinc presumably would limit its usefulness during the 1-2 minutes of consumer brushing.

In some embodiments, the present invention provides polymer matrix films comprising: one or more cellulose polymers, and colloidal particles. In some embodiments, the colloidal particles are present in an amount between 40% and 50% of the polymer matrix film's dry weight. In some embodiments, the one or more cellulose polymers comprise between 40% and 50% of the polymer matrix film's dry weight. In some embodiments, the colloidal particles are zinc oxide particles.

In some embodiments, the colloidal particles comprise water-insoluble metal compounds of multivalent metals. In some embodiments, the colloidal particles suitable for use in the compositions described herein comprise silicon oxide ($SiO_2$), molybdenum oxide ($Mo_2O_3$), aluminum oxide ($Al_2O_3$), titanium oxide (TiO), or zirconium oxide ($ZrO_2$).

In other embodiments, the one or more cellulose polymers and the colloidal particles comprise between 80% and 95% of the polymer matrix film's dry weight.

In some embodiments, the films of the present invention comprise less than 8% canola oil. In other embodiments, the films are substantially free of canola oil.

In some embodiments, at least one of the one or more cellulose polymers is a hydroxyalkyl methyl cellulose. In further embodiments, at least one of the one or more cellulose polymers is hydroxypropyl methyl cellulose (HPMC). In some embodiments, at least one of the one or more cellulose polymers is HPMC and the colloidal particles are zinc oxide particles.

HPMC is the preferred backbone polymer for use in the present invention, and is the backbone polymer system presently employed in some commercially available MaxFresh products. HPMC is a long-chained, nonionic polymer and its mucoadhesion is attributed to formation of hydrogen bonding with mucus components.

Even though HPMC exhibits mucoadhesion, it is not considered one of the best mucoadhesive polymers (Majithiya, R., et. al; Drug Delivery Technology; Vol. 8 (2008) 40-45). One hypothesis for the hydration of HPMC and its impact on binding can be categorized into 3 stages:

1. At low water concentrations, films begin to hydrate for binding to occur.
2. At ideal water concentrations, films are fully hydrated and maximum binding occurs.
3. At higher water concentrations, films become over hydrated and begin to dissolve away.

One hypothesis for zinc oxide binding is that water insoluble metal oxides (zinc oxide) enhance the bioadhesive properties of polymers (HPMC). Ionic interactions occur between the partially ionized divalent or trivalent cations on the surface of the metal particles to negatively charged mucin chains (glycosubstances). See Vasir, J., et. al; International Journal of Pharmaceutics; Vol. 255 (2003) 13-32; Jacob, J., et. al, U.S. Pat. No. 6,123,965, the disclosure of which is incorporated by reference herein in its entirety. These interactions are believed to help make the ZnO films mucoadhesive in the oral cavity. Varying the polymer system and incorporating greater amounts of zinc-containing compounds into the oral composition enables an increase in the amount of zinc to levels that are commensurate with currently marketed zinc citrate formulations, which have been clinically proven to have antiplaque and anti-gingivitis efficacy.

The oral compositions of the preferred embodiments include a zinc-containing compound in a film that provides a source of zinc ions. The zinc-containing compound can be a soluble or sparingly soluble compound of zinc with inorganic or organic counter ions. Examples include the fluoride, chloride, chlorofluoride, acetate, hexafluorozirconate, sulfate, tartrate, gluconate, citrate, lactate, malate, glycinate, pyrophosphate, metaphosphate, oxalate, phosphate, carbonate salts, and oxides of zinc. Preferably, the zinc-containing compound is zinc oxide, and is used as a replacement for conventional anti-bacterial agents such as triclosan.

The amount of zinc-containing compound included in the film can vary from about 35% to about 60% by weight, preferably from about 40% to about 55%, and most preferably about 50% by weight. The amount of film included in the oral composition also can vary anywhere from about 0.1% to about 5.0%, more preferably from about 0.25% to about 3.0%, and most preferably from about 0.5% to about 2.0% by weight film. The amount of zinc-containing compound employed in the overall oral composition therefore can vary from about 0.5 to about 2.5 wt %, based on the total weight of the composition, typically from about 1 to about 2 wt %, based on the total weight of the oral care composition.

In some embodiments, the films further comprise one or more additional components selected from the group consisting of: diols, surfactants, starches, colorants, dyes, flavor agents, sweeteners, whitening agents, breath freshening agents, abrasives, cationic prophylactic and therapeutic agents, fluoride ion sources, stannous ion sources, tartar control agents, antimicrobial agents, antioxidants, saliva stimulating agents, antiplaque agents, anti-inflammatory agents, H2 antagonists, desensitizing agents, nutrients, and proteins.

In some embodiments, the films further comprise polysorbate 80 and/or propylene glycol. In some embodiments, the films comprise from about 40% to about 50% HPMC; from about 40% to about 50% zinc oxide particles; from about 7.5% to about 9& propylene glycol; and from about 1.25% to 1.5% polysorbate 80.

Some embodiments provide methods of making the films described herein, comprising the steps of: forming a slurry comprising one or more cellulose polymers, and colloidal particles, dispensing the slurry on a surface wherein the slurry forms a layer of slurry on the surface, and drying the layer of slurry to remove solvent and produce a polymer matrix film. Some embodiments further comprise the step of cutting or punching the polymer matrix film to form film flakes or strips. Yet other embodiments provide a dentifrice composition comprising an orally acceptable vehicle, and any of the films described herein. In some embodiments, the film is in the form of film flakes or strips.

In some embodiments, the zinc-containing compound is present in the form of particles. In some embodiments, the particles have an average particle size of about 1 to about 1000 nm. In other embodiments, the particles may have an average particle size from about 1 μm to about 850 nm, about 50 μm to about 150 nm, about 15 nm to about 500 nm, about 30 nm to about 250 nm and/or about 5 μm to about 100 nm.

In some embodiments, the particles are non-aggregated. By non-aggregated it is meant that the particles are not massed into a cluster having a size greater than about 1 micron, preferably greater than about 950 nm or 850 nm. However, in further embodiments, particles may be mixed with aggregated particles and other colloidal particles that have an average particle size of greater than 1 micron. In some embodiments, more than 80% of particles are non-aggregated. In some embodiments, more than 90% of particles are non-aggregated.

Zinc ions are derived from the zinc-containing compound present in the film in the dentifrice composition in an effective amount. An effective amount of zinc ions is defined as from at least 1000 ppm zinc ion, preferably 2,000 ppm to 15,000 ppm. More preferably, zinc ions are present in an amount from 3,000 ppm to 13,000 ppm and even more preferably from 4,000 ppm to 10,000 ppm. This is the total amount of zinc ions that is present in the compositions for delivery to the tooth surface.

Examples of suitable zinc-containing compounds that serve as zinc ion sources are zinc oxide, zinc sulfate, zinc chloride, zinc citrate, zinc lactate, zinc gluconate, zinc malate, zinc tartrate, zinc carbonate, zinc phosphate, and other salts listed in U.S. Pat. No. 4,022,880.

The zinc-containing compound can be incorporated into the film using techniques known in the art. For example, the zinc-containing compound can be formed in a slurry with the polymer or polymer mixture forming the film, together with additives such as propylene glycol, Polysorbate 80 (Tween 80), water, flavorants, colorants, and the like, and the slurry dried to form a film. Other methods of making the film are known and described in, for example, U.S. Pat. No. 6,669,929, and U.S. Patent Application Publication No. 2003/0053962, the disclosures of which are incorporated by reference herein in their entirety. It is preferred that the zinc-containing compound is zinc oxide, and is present in the dried film in an amount of about 50% by weight, based on the total weight of the film.

Physical characteristics of the film containing the relatively high concentration of zinc-containing compounds can be modified by modifying various parameters of the film forming process. These parameters can be determined by quantifying the properties of the film at both the slurry stage and the dry film stage. At the slurry stage, the interactions between the polymers and the other film ingredients form the structure of the film matrix. The viscoelastic properties of the slurry, such as the viscosity and the elastic modulus (G'), enable the characterization of the polymer structure and the processability of the slurry. Following processing and drying of the slurry, the bulk film can be formed, setting the polymer matrix. Mechanical properties, such as the glass transition temperature, the tensile strength, and the dissolution time can be used to determine the stability of the film. By balancing the microstructural properties, such as the polymer interactions, with the macrostructural properties of the film, such as the mechanical properties, films can be better utilized as a delivery platform for the zinc-containing compounds.

For example, the films preferably can be dissolved in the oral cavity of a subject. Dissolution time is the amount of time needed to dissolve a piece of film in a stagnant volume of water. Films having rapid dissolution times sometimes have low tensile strength because they are rapidly disintegrated. Characteristics of the film, such as tensile strength and dissolution time, therefore can be tailored during the formulation process based on the requirements of the final product. A person having ordinary skill in the art will appreciate that a balance exists between these two properties to specifically formulate a robust film that can withstand processing and still dissolve readily in the mouth.

For example, the inventors carried out experiments to determine the effects of zinc loading on the resultant film. At higher concentrations of zinc-containing compound, the polymer structure becomes too rigid, and the viscoelastic properties of the film, (e.g., elastic modulus G'), increased dramatically. It was found that the value of G' (dynes/cm$^2$) sharply increased at concentrations of zinc above 50% by weight, based on the final weight of the film. The inventors further found that increasing the amount of zinc-containing compound above 50% rendered the slurry difficult to handle, and not as flowable as lower concentrations. Above 50% zinc loading, the shape of the flow curve (shear rate vs. viscosity), changes dramatically, indicating the dominance of the ZnO particle-particle interactions, which disrupt the polymer network.

The mechanical properties of the resulting film also can be used to determine physical stability. For example, films containing 50% zinc oxide by weight had higher glass transition temperatures than films containing 30% zinc oxide by weight. Accordingly, films containing the higher amount of zinc-containing compound were stronger. In addition, the storage modulus (E'), which measures the stiffness of the film, indicates that as the amount of ZnO is increased from 30% to 50%, the strength of the film also increases. The higher E' determined in the examples below supports this conclusion. In general, ZnO is a filler that adheres to the polymer in a process known as steric stabilization. In the absence of ZnO, the polymer motion is unrestricted, which can lead to cosmetic instability, such as curling. As ZnO is added, the polymer network becomes restricted, causing the film to stiffen. However, the addition of more than 50% ZnO would disrupt the polymer structure, resulting in the film becoming brittle and crack. These mechanical properties correlate with the other physical properties as an increase in ZnO, up to 50%, equates to a stiffer, stronger, and more stable film. Tensile strength of 50% zinc oxide films also were improved, when compared to 30% zinc oxide films.

The compositions of the embodiments may be described as comprising two phases, wherein one phase comprises a carrier and a second phase comprises the aforementioned film or fragment. The term "phase" as used herein denotes a physical phase as understood in the physical and material sciences, i.e., a portion of a material whose properties and composition are uniform. However, a phase as used herein can be discontinuous, i.e., a phase can comprise a plurality of separate components. For example, a plurality of polymer film fragments of identical composition is considered to comprise a single phase. In some embodiments, a film fragment can be entirely embedded within the material comprising the first phase, or totally or partially exposed on the surface of the first phase. For example, if the composition is a dentifrice comprising both a gel and film fragments, a film fragment can be totally surrounded by the gel, or partially or totally exposed on the surface of the gel. In certain embodiments, compositions comprise more than two phases. Such multi-phase compositions include those having two carriers, each of which contributes a phase to the composition, in addition to film fragments as described herein. Other multi-phase compositions include those having a single carrier and two or more pluralities of fragments, wherein the pluralities of fragments have differing compositions.

In various embodiments, the carrier is a liquid, semi-solid or solid. A "liquid" can be a liquid of low or high viscosity. A liquid can be a liquid such that flow is imperceptible under ambient conditions. For example, a soap, such as an ordinary bar of hand soap, can be considered a liquid herein. A liquid can be a thixotropic liquid. A "semi-solid" as used herein can be a gel, a colloid, or a gum. As used herein, semi-solids and liquids are fluids distinguished on the basis of viscosity: a semi-solid is a high viscosity fluid, while a liquid has lower viscosity. There is no definitive dividing line between these two types of fluids. A semi-solid can, in certain embodiments, have a viscosity as high as thousands of mPa·s. Carriers among those useful herein include liquids, pastes, ointments, and gels, and can be transparent, translucent or opaque.

In certain embodiments, the compositions of the present invention are oral care compositions, suitable for administration to the oral cavity. Such compositions include dentifrices, mouthwashes, dental gels, lozenges, beads, gums, oral strips, mints, liquid toothpastes, sprays, paint-on gels, lip balms, whitening strips, breath strips, oral chews, and combinations thereof. An oral care composition disclosed herein can be used, for example, for cavity prevention, whitening, plaque prevention or reduction, gingivitis prevention or reduction, tartar control, sensitivity prevention or reduction, or breath malodor prevention or reduction, and stain prevention.

The specific composition of the carrier preferably depends on the intended use of the composition. In various embodiments, the carrier is aqueous, comprising from about 5% to about 95% water or from about 10% to about 70% water. In other embodiments, the carrier is substantially non-aqueous. In a dentifrice carrier, water content can be from about 5% to about 70%, from about 10% to about 50%, or from about 20% to about 40%. When the presence of water will cause the film to disintegrate, it is particularly preferred that the dried film contain no free water, in which the amount of water is substantially 0%, or negligible.

The carrier may comprise any of a variety of materials, including emulsifiers, thickeners, fillers, and preservatives. In some embodiments, the carrier may include a functional or active material, such as those described above. In some embodiments, the carrier comprises the same functional material as the film.

In one embodiment, the carrier is suitable for use as a dentifrice. In some embodiments, the carrier comprises a humectant, such as glycerine, sorbitol or an alkylene glycol such as polyethylene glycol or propylene glycol. In some configurations, the carrier comprises a humectant at a level of from about 10% to about 80% by weight, or about 20% to about 60% by weight of the composition. Carrier compositions among those useful herein are disclosed in U.S. Pat. No. 5,695,746, Garlick, Jr., et al, and U.S. Pat. No. 4,839,157, Mei-King Ng et al.

In various dentifrice embodiments, the carrier comprises thickeners, gelling agents or combinations thereof. Thickeners or gelling agents useful herein include inorganic, natural or synthetic thickeners or gelling agents. In some configurations, the carrier comprises the thickener and gelling agent at total levels of from about 0.10% to about 15% by weight, or from about 0.4% to about 10% by weight of the composition. Examples of thickeners and gelling agents useful herein include inorganic thickening silicas such as: amorphous silica, for example Zeodent® 165 (Huber Corporation); Irish moss; iota-carrageenan; gum tragacanth; or polyvinylpyrrolidone. In certain embodiments, the carrier comprises a polishing agent, such as a silica, a calcined alumina, sodium bicarbonate, calcium carbonate, dicalcium phosphate or calcium pyrophosphate. In various embodiments, the carrier can be a visually clear composition.

In various dentifrice embodiments, comprising a visually clear carrier, the composition comprises at least one polishing agent. Polishing agents among those useful herein include collodial silica, such as, for example, Zeodent® 115 (Huber Corporation), and alkali metal aluminosilicate complexes (i.e., a silica comprising alumina). In some configurations, a polishing agent can have a refractive index close to that of a gelling agent combined with water and/or humectant. In various embodiments, the carrier comprises the polishing agent at a level of from about 5% to about 70% by weight of the composition.

In certain dentifrices, the carrier comprises a surfactant or mixture of surfactants. Surfactants among those useful herein include water-soluble salts of at least one higher fatty acid monoglyceride monosulfate, such as the sodium salt of the monsulfated monoglyceride of hydrogenated coconut oil fatty acids; cocamidopropyl betaine; a higher alkyl sulfate such as sodium lauryl sulfate; an alkyl aryl sulfonate such as sodium dodecyl benzene sulfonate; a higher alkyl sulfoacetate; sodium lauryl sulfoacetate; a higher fatty acid ester of 1,2-dihydroxy propane sulfonate; and a substantially saturated higher aliphatic acyl amides of a lower aliphatic amino carboxylic acid, such as those having 12 to 16 carbons in the fatty acid, alkyl or acyl radicals; and mixtures thereof. Amides can be, for example, N-lauroyl sarcosine, and the sodium, potassium, and ethanolamine salts of N-lauroyl, N-myristoyl, or N-palmitoyl sarcosine. In various embodiments the carrier comprises the surfactant at a level of from about 0.3% to about 5% by weight of composition, or about 0.5% to about 3% by weight of composition.

The present invention also provides methods for making a dentifrice carrier. In one embodiment, water and at least one humectant are dispersed in a conventional mixer until a first homogeneous gel phase is formed. A polishing agent is added into the first homogeneous gel phase. The first homogeneous gel phase and the polishing agent are mixed until a second homogeneous gel phase is formed. A thickener, flavorant and surfactants are added to the second homogeneous gel phase. These ingredients are mixed at high speed under vacuum of about 20 to 100 mmHg.

The compositions of the present invention are preferably stable under normal conditions of storage. As referred to herein, "stable" refers to the lack of significant adverse effect on one, and preferably all, compositional attributes such as appearance, flavor, rheology, and chemical composition of the composition. Preferably, stability in the present compositions includes the compositional and physical stability of film (including fragments, if any) in the composition. In various embodiments a composition comprising a film is stable upon storage at ambient temperature for at least about two years. It is understood, however, that in some embodiments, an otherwise stable film can disintegrate during use (as discussed above), for example, during toothbrushing using a dentifrice composition.

In certain embodiments, a composition can comprise, in addition to film fragments as described herein, two or more carriers, each of which contributes a phase to the composition. Such a composition can be stable to color bleeding. For example, a composition can include film fragments and a striped dentifrice such as that disclosed in U.S. Pat. No. 6,315,986, Wong et al. In certain embodiments, the film fragments can be of different color(s) than the stripe(s) for enhanced aesthetic appeal.

The embodiments also provide processes for making compositions comprising a film entrained in a carrier. In various embodiments, a plurality of fragments are combined with a carrier. In some configurations, a carrier and a plurality of film fragments can be mixed. In some configurations, the mixing can comprise slow stirring. In one preferred embodiment, the process for making the composition comprising a carrier having distributed therein a plurality of lamellar fragments includes:

(a) providing the carrier;

(b) adding lamellar fragments of a film containing a relatively high concentration of zinc-containing compound to the carrier to form a mixture; and (c) homogenizing the mixture.

The term "homogenizing" as used herein refers to the admixture of the fragments and the carrier so as to attain a substantially homogeneous distribution of fragments in the carrier. It should be noted, however, that the resulting composition still retains two-phase composition characteristics. Homogenizing may be accomplished using any of a variety of conventional homegenizers.

In another method, the film is added to a component of the carrier (e.g., to a humectant for a dentifrice). The remainder of the carrier then may be made, and the mixture of film then added to the carrier.

Certain embodiments described herein also provide methods for administering a zinc-containing compound to a human or animal subject. As referred to herein, "administering" refers to any method by which a composition is applied on or administered to the subject. In various embodiments, the administration is topical, wherein the composition is applied to an external surface of the subject, such as to a surface of the oral cavity (e.g., teeth, gingiva, and tongue). The specific route and method of administration will depend, of course, on the intended use of the composition.

In various embodiments, the present invention provides methods for administering a zinc-containing compound to a human or animal subject in need thereof, comprising topically applying to said subject a composition comprising a film entrained in a carrier, wherein the film includes a relatively high concentration of zinc-containing compound. In one embodiment, the method additionally comprises disrupting the film after topically applying the film. Such disruption may be accomplished by any of a variety of methods, including chemical and/or mechanical means. Chemical means include degradation of the film by contact with water or a material present at the site of administration (e.g., saliva in an oral care application). Physical means include agitation, grinding, and shear forces produced by application of physical energy to the composition during use (e.g., brushing in a dentifrice application).

In various embodiments, the present invention provides methods for the treatment of an oral care condition. As referred to herein, an "oral care condition" is any disorder or condition which can be prevented or treated by administration of a composition to the oral cavity, including disorders or conditions of the teeth, oral mucosa, gingiva and tongue. Such conditions include caries, gingivitis, periodontitis, and cosmetic conditions such as yellowing and malodour.

The embodiments described herein can be further understood by reference to the following non-limiting examples.

EXAMPLES

Example 1

This example illustrates various methods of making polymeric films containing varying amounts of zinc oxide. A currently available commercial film product containing 30% by weight zinc oxide (commercially available in MaxFresh Nite® formulations, available from Colgate-Palmolive Company, New York, N.Y.) also is shown in Table 1 below.

TABLE 1

30% Zinc Oxide Film Formula

| Raw Materials | Slurry Wt. % | Dry Wt. % |
|---|---|---|
| Water | 71.16 | — |
| Methocel E5 | 10.3 | 35.714 |
| Methocel E50 | 3.1 | 10.749 |
| Zinc Oxide | 8.76 | 30.374 |
| Propylene Glycol | 6.18 | 21.429 |
| Tween 80 | 0.5 | 1.734 |

TABLE 2

40% Zinc Oxide Film Formula

| Raw Materials | Slurry Wt. % | Dry Wt. % |
|---|---|---|
| Water | 69.57 | — |
| Methocel E5 | 9.36 | 30.759 |
| Methocel E50 | 2.82 | 9.267 |
| Zinc Oxide | 12.2 | 40.092 |
| Propylene Glycol | 5.6 | 18.403 |
| Tween 80 | 0.45 | 1.479 |

TABLE 3

50% Zinc Oxide Film Formula

| Raw Materials | Slurry Wt. % | Dry Wt. % |
|---|---|---|
| Water | 66.52 | — |
| Methocel E5 | 8.58 | 25.627 |
| Methocel E50 | 2.58 | 7.706 |
| Zinc Oxide | 16.74 | 50.0 |
| Propylene Glycol | 5.16 | 15.412 |
| Tween 80 | 0.42 | 1.254 |

TABLE 4

60% Zinc Oxide Film Formula

| Raw Materials | Slurry Wt. % | Dry Wt. % |
|---|---|---|
| Water | 49.72 | — |
| Methocel E5 | 10.3 | 20.485 |
| Methocel E50 | 3.1 | 6.165 |
| Zinc Oxide | 30.2 | 60.064 |
| Propylene Glycol | 6.18 | 12.291 |
| Tween 80 | 0.5 | 0.994 |

It was found that the 60% zinc oxide film formulation was not robust and too brittle to form into a useable film. This unsuitable film was visually evident during the drying process of the film when the film was cracked. While such a film could be used to formulate a suitable oral care composition, it is preferred not to use the film in commercial operations since its physical characteristics would make it difficult to process on a commercial scale. Examples below further illustrate how varying amounts of zinc oxide in the slurry affect the film forming properties, as well as the resulting film properties.

Example 2

This example illustrates the effect of ZnO particles on the rheological properties of the film slurries. Film slurries were made varying the concentration of ZnO and deionized water while the HPMC, propylene glycol, and polysorbate 80 were held constant. The amount of ZnO in the slurries was based on dry film concentrations of 0%, 30%, 40%, 45.5%, 50%, 55%, and 60% ZnO. The slurry compositions are shown in Table 5.

TABLE 5

| Ingredients | Supplier | ZnO in Dry Film | | | | | | |
|---|---|---|---|---|---|---|---|---|
| | | 0% | 30% | 40% | 45.5% | 50% | 55% | 60% |
| HPMC E5 | Dow Chemical | 8.57 | 8.57 | 8.57 | 8.57 | 8.57 | 8.57 | 8.57 |
| HPMC E50 | Dow Chemical | 4.29 | 4.29 | 4.29 | 4.29 | 4.29 | 4.29 | 4.29 |
| Zinc Oxide (AZO 66USP) | US Zinc | 0.00 | 6.68 | 10.39 | 12.99 | 15.58 | 19.05 | 23.37 |
| Propylene Glycol | Univar | 2.34 | 2.34 | 2.34 | 2.34 | 2.34 | 2.34 | 2.34 |
| Polysorbate 80 | Croda | 0.39 | 0.39 | 0.39 | 0.39 | 0.39 | 0.39 | 0.39 |
| Water (DI) | — | 84.42 | 77.74 | 74.03 | 71.43 | 68.83 | 65.37 | 61.04 |
| Total (%) | — | 100 | 100 | 100 | 100 | 100 | 100 | 100 |

The slurries were prepared by heating deionized water to about 80° C. About half of the formula amount of water was added to beaker. Next, HPMC E5 was added and mixed with an overhead mixer until the polymer was wet. HPMC E50 was then added and the slurry was mixed for 20 min with intermittent scraping of the beaker walls to ensure polymer incorporation. The ZnO powder was then added along with the remaining amount of water. After 15 min of mixing, the propylene glycol and the polysorbate 80 were added. The slurry was complete after an additional 20 min mixing. Prior to the performance of rheology experiments, air bubbles in the slurries were removed by mixing with the SpeedMixer™ DAC 150 FVZ for 5 min at 1800 rpm.

The rheological measurements were conducted using the AR2000ex rheometer from TA Instruments with the concentric cylinder conical DIN geometry. Viscoelastic properties, such as the elastic modulus (G') and the loss modulus (G"), were obtained from strain sweep experiments. For the strain sweep measurements, the angular frequency was held at 1 Hz while the strain varied from 0.1 to 500%. Viscosity measurements were obtained from steady state flow experiments, which were conducted varying the shear rate from 100 to 0.1 $s^{-1}$. The effect of the elastic modulus (G') of the film slurries as a function of zinc oxide concentration is shown in FIG. 1. The effect of zinc ion concentration on viscosity as a function of shear rate is shown in FIG. 2.

In addition to G', the viscosity profile as a function of shear rate was used to quantify the effect of ZnO concentration on the flowability and ultimately, the processability, of the slurries. In general, as the ZnO concentration increases, the viscosity increases as well (FIG. 2). At ZnO concentrations of up to 40%, the shapes of the viscosity profiles are similar and they are typical of a semi-dilute solution. In these slurries, the polymer-polymer interactions are dominant and the particles play a lesser role; therefore, the slurries are liquid-like and very flowable. At 45.5 to 50% ZnO loading, the shape of the flow curve changes slightly, and an increase in viscoelasticity is observed. This increase in viscosity is driven primarily by ZnO-polymer interactions and more specifically, by the restricting effect that the colloidal particles have on the polymer chains. Above 50% ZnO loading, the viscosity profiles change dramatically, indicating the dominance of the ZnO particle-particle interactions, which disrupt the polymer network.

As an increasing amount of ZnO is added, the increase in G' signifies the strengthening of the structural network of the film. However, the polymer structure becomes too rigid above 50% ZnO loading, as indicated by the dramatic increase in G', to maintain the integrity of the film. The viscosity profile as a function of shear rate was used to quantify the effect of ZnO concentration on the flowability and ultimately, the processability, of the slurry. In general, as the ZnO concentration increases, the viscosity increases as well.

Figure 2:
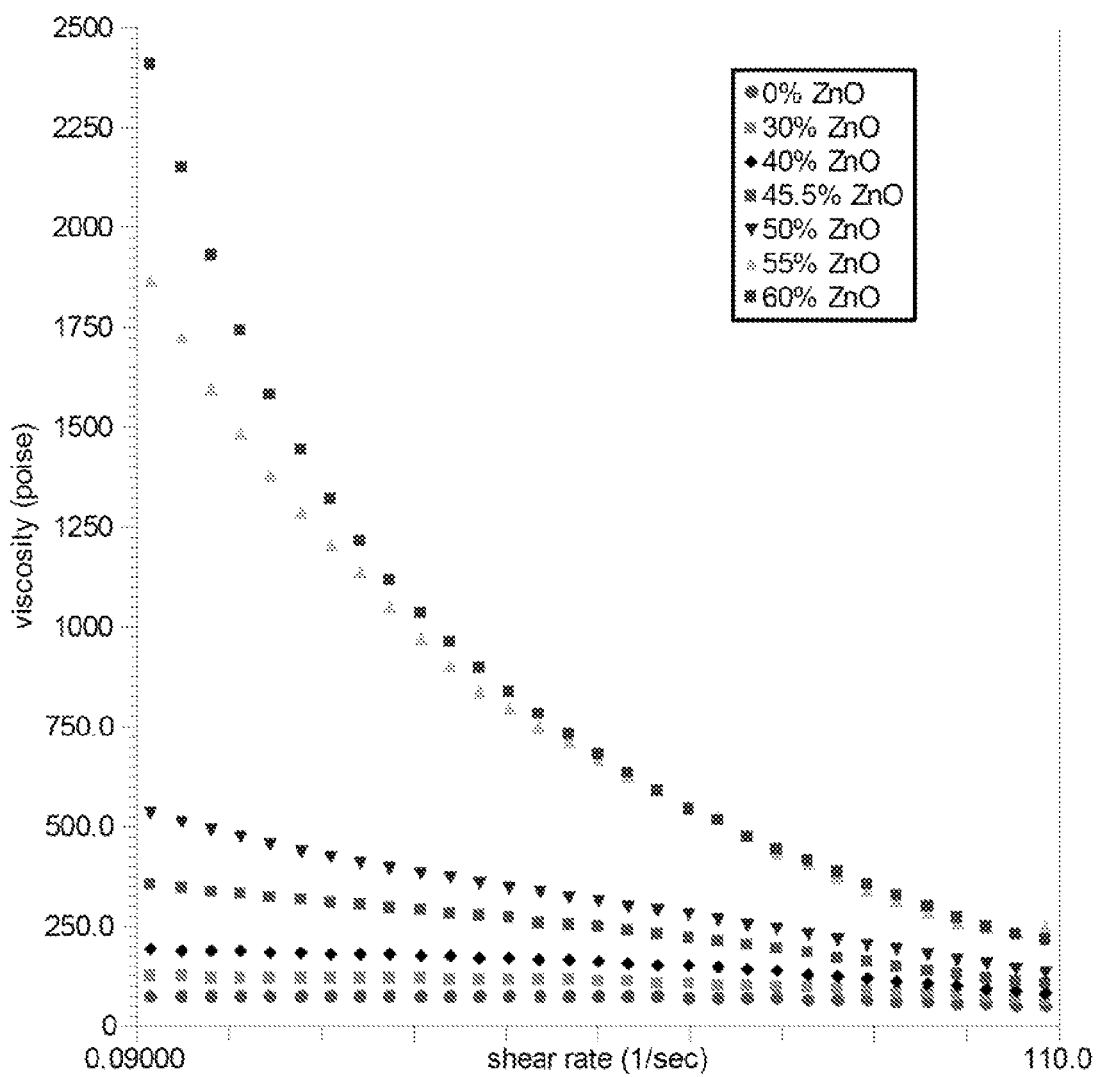
FIG. 2 shows the effect of zinc ion concentration on viscosity as a function of shear rate, as prepared in accordance with Example 2.

At ZnO concentrations of up to 40%, the shapes of the flow curves shown in FIG. 2 are similar and they are typical of a semi-dilute solution. In these slurries, the polymer-polymer interactions are dominant. At 45.5 to 50% ZnO loading, the shape of the flow curve changes slightly, showing the increasing effect of ZnO-polymer interactions. Above 50% ZnO loading, however, the curves change dramatically, indicating the dominance of the ZnO particle-particle interactions, which disrupt the polymer network. In addition, the viscosities of the slurries above 50% ZnO loading are very high, limiting manufacturing processability. Therefore, based on the viscoelastic properties, 50% ZnO loading would appear to be the preferred concentration to provide the flowability and the structural integrity needed for processing into a stable film.

Example 3

Just as rheology can be used to characterize the slurries that are precursors to the films, the mechanical properties of the films themselves can be measured using a Dynamic Mechanical Analyzer to determine the physical stability of various films. In this experiment, the films tested were a film containing 30% by weight zinc oxide and a film containing 50% by weight zinc oxide. From the glass transition temperature (Tg), which is the temperature at which the film softens, the 50% ZnO film was found to be stronger than the 30% ZnO film due to its higher Tg (Table 6).

TABLE 6

$T_g$ and E' (at 1 Hz) for 30% and 50% ZnO films.

| Film | $T_g$ (° C.) | E' (MPa) at 1 Hz |
|---|---|---|
| Zn30 | −55.6 | 1300 |
| Zn50 | −32.1 | 1800 |

In addition, the storage modulus (E'), which measures the stiffness of the film, indicates that as the amount of ZnO is increased from 30% to 50%, the strength of the film also increases. The higher E' supports this conclusion. In general, ZnO is a filler that adheres to the polymer in a process known as steric stabilization. In the absence of ZnO, the polymer motion is unrestricted, which can lead to cosmetic instability, such as curling. As ZnO is added, the polymer network becomes restricted, causing the film to stiffen. However, the addition of more than 50% ZnO would disrupt the polymer structure, resulting in the film becoming brittle and crack. These mechanical properties correlate with the other physical properties as an increase in ZnO, up to 50%, equates to a stiffer, stronger, and more stable film.

Example 4

The tensile strength and dissolution time are physical characteristics that describe the film properties and robustness. Table 7 shows the physical properties measured for film containing 30% by weight zinc oxide (Zn30) and a film containing 50% by weight zinc oxide (Zn50).

TABLE 7

| Test | Zn30 Film | Zn50 Film |
|---|---|---|
| Thickness* | 0.00138 in | 0.00105 in |
| Tensile Strength | 3,348 psi | 4,127 psi |
| Dissolution Time | 26 sec | 34 sec |

*Key specification of films that can affect the tensile strength and dissolution time.

These results are acceptable based on the balance that exists between the breaking strength and dissolution time to formulate a robust film that can withstand processing and still dissolve readily in the mouth.

Example 5

Zinc uptake experiments were performed to compare the amount of zinc delivered to an artificial soft substrate using the same level of zinc oxide films in toothpaste with different loadings. The films (Zn30 and Zn50) were incorporated into a MaxFresh Nite toothpaste base. The experiments included comparing:
  1. Zn30 and Zn50 at 0.2% film concentration;
  2. Comparison of Zn50 film versus equivalent ZnO powder; and
  3. Zn50 at different film concentrations.
Certain parameters for testing were kept constant for the experiments. They included:
  Vitro-Skin incubated for 1 hour
  1:2 dilution of toothpaste to deionized water
  Two 5 mL washes of deionized water for 10 seconds
1. Zn30 and Zn50 at 0.2% Film Concentration
Toothpaste samples were provided by product development for evaluation. The Zn30 and Zn50 films were tested at 0.2% film concentrations with a positive control of MaxFresh Nite and a negative control of MaxFresh film. The zinc uptake results are seen on Table 8.

TABLE 8

| Sample | ppm | $\mu g/cm^2$* |
|---|---|---|
| 0.2% MaxFresh Film (control) | 0 | 0.0 |
| 0.2% Zn30 Film | 12.7 | 35.3 |
| 0.2% Zn50 Film | 23.6 | 65.6 |
| 0.5% Zn30 Film (MaxFresh Nite) | 29.8 | 82.8 |

*Dilution of sample over area of substrate.

The results clearly show that twice as much zinc is delivered from Zn50 film versus Zn30 at the same film concentration. When comparing Zn30 versus Zn50, the binding is similar with Zn50 delivering more zinc. This can be due to the high loading nature of the Zn50 film.

One hypothesis for zinc oxide binding is that water insoluble metal oxides (zinc oxide) enhance bioadhesive properties of polymers (HPMC). Ionic interactions occur between the partially ionized divalent or trivalent cations on the surface of the metal particles to negatively charged mucin chains (glycosubstances). These interactions help to make the ZnO films mucoadhesive in the oral cavity.

2. Comparison of ZnO Film Versus Equivalent ZnO Powder

An experiment was performed to analyze the amount of zinc delivered from ZnO films in toothpaste versus the same concentration of ZnO powder in toothpaste. The samples tested and the zinc uptake results are seen in Table 9.

TABLE 9

| Sample | Ppm | $\mu g/cm^2$ |
|---|---|---|
| 0.3% Zn50 Film | 32.15 | 89.3 |
| 0.15% ZnO Powder | 2.05 | 5.7 |
| 2.0% Zn50 Film | 337 | 936.1 |
| 1.0% ZnO Powder | 59.7 | 21.5 |

The data described in Table 9 demonstrate that more zinc is delivered from the ZnO film than from its equivalent in a ZnO powder. At both high and low ZnO percentages, 15 times more zinc is delivered from the film versus ZnO powder. While not intending to be being bound by any theory of operation, the inventors believe that the film may be acting as a delivery system to deposit more zinc onto the soft substrate.

3. Zn50 at Different Film Concentrations

An experiment was performed to analyze different film concentrations for Zn50 films in toothpaste to see a dose response. The samples tested and the zinc uptake results are seen in Table 10.

TABLE 10

| Sample | ppm | $\mu g/cm^2$ |
|---|---|---|
| 0.2% Zn50 | 23.6 | 65.6 |
| 0.3% Zn50 | 32.15 | 89.3 |
| 0.5% Zn50 | 59.75 | 166.0 |
| 1.0% Zn50 | 165.5 | 459.7 |
| 2.0% Zn50 | 337 | 936.1 |

As shown in Table 10, increasing the film concentration in toothpaste does increase the amount of Zn delivered to the soft substrate. There also was an increase in binding with an increase in film concentration. The zinc uptake method quantifies the amount of zinc delivered to a soft substrate. Vitro-Skin was used as a model substrate because it mimics human skin. The zinc uptake results show that increasing film concentration of Zn50 films increases the zinc uptake. Also the films act as a delivery vehicle to deposit more zinc onto the substrate than its equivalent in powder form.

Example 6

A laboratory test was performed on the Zn30 and Zn50 film strips versus a MaxFresh menthol film control to determine the reduction of VSCs overnight. The results of this laboratory test are described in Table 11 (below). The overnight VSC results show that the Zn50 film at 0.2% and 0.5% film concentrations show a higher reduction in VSCs compared to same film levels of Zn30 film. This shows that higher reduction of VSCs can be obtained with the same concentration of films if we load up the concentration of actives in the film.

TABLE 11

| Strip Sample | % Reduction |
|---|---|
| 0.2% Men | 1.85 |
| 0.2% Zn30 | 12.15 |
| 0.2% Zn50 | 26.39 |
| 0.5% Zn30 | 22.19 |
| 0.5% Zn50 | 54.19 |

Another laboratory test was performed to test the reduction of VSCs from full toothpaste formulations. Samples tested were: Current MaxFresh toothpaste, 0.2% Zn50 films in TP, 0.2% Zn30 films in TP, Crest+Scope, Close Up, Aqua Fresh and Total. The results of this laboratory test are described in Table 12 (below). From the results, although both zinc oxide film formulas showed strong performance versus standard fresh breath formulas, the higher loading zinc oxide film (Zn50) performed better than the Zn30 at the same concentration.

TABLE 12

| Sample | % Reduction |
|---|---|
| Current MF | 4.5 |
| MF + 0.2% Zn50 | 70.7 |
| MF + 0.2% Zn30 | 42.5 |
| Crest + Scope | 7.2 |
| Close Up | 7.5 |
| Aqua Fresh | 10.1 |
| Total | 95 |

Example 7

A clinical test was performed to evaluate the reduction of total cultivated bacteria with the higher loading of zinc oxide film (50%) at 0.2% versus MaxFresh with menthol film. The results of the clinical test are described in Table 13 (below). The results show that the higher loading zinc oxide film (50%) is effective at reducing bacteria at 2 hour, 4 hour, and overnight even at relatively low doses.

All zinc uptake evaluations showed that more zinc is delivered from the Zn50 films than the Zn30 or ZnO powder equivalents. This means that not only can more zinc be delivered from the higher loading film to enhance efficacy but also a lower amount of film is required which can reduce the cost of the final product.

TABLE 13

Reduction of Total Cultivable Salivary Bacteria, log (CFU)

| Test Product | PIM# | 2 h | SE 2 h | 4 h | SE 4 h | Overnight | SE Overnight |
|---|---|---|---|---|---|---|---|
| MaxFresh (1450 ppm NaF) Toothpaste with 0.2% ZnO | 417248 | 0.475 | 0.106 | 0.224 | 0.111 | 0.1019 | 0.0756 |
| Strip (1450 ppm NaF) | 422915 | 0.812 | 0.105 | 0.551 | 0.105 | 0.26 | 0.0955 |

Example 8

The viscosity of the slurries above 50% ZnO loading is very high, limiting manufacturing processability and giving rise to very brittle films with little flexibility. Therefore, based on the viscoelastic properties, one can determine the optimal film composition to provide the flowability and the structural integrity needed for processing a stable film. Essentially, a particle loading between 0-40% will result in a very flexible film, a loading between 40-50% will result in a semi-flexible film, and a loading >50% will result in a very rigid, brittle film. The expected ranges for G' and viscosity (taken at 0.3 s$^{-1}$) for the various slurries are tabulated in Table 14 (below).

TABLE 14

| ZnO concentration (%) | G' (dyne/cm$^2$) | Viscosity (poise) (at 0.3 s$^{-1}$) |
|---|---|---|
| 0-40 | 48-223 | 70-183 |
| 40-50 | 223-550 | 183-450 |
| >50 | 550-2300 | 450-1500 |

Each of the patents, patent applications and printed publications (including books) mentioned in this document are hereby incorporated by reference in their entirety.

As those skilled in the art will appreciate, numerous changes and modifications may be made to the embodiments described herein without departing from the spirit of the invention. It is intended that all such variations fall within the scope of the appended claims.

The invention claimed is:

1. An oral care composition comprising:
    a film entrained in a carrier, wherein said film comprises a zinc-containing compound in an amount of from about 40% by weight to about 55% by weight, of the film;
    wherein said zinc-containing compound is selected from the group consisting of: zinc oxide; zinc sulfate; zinc chloride; zinc citrate; zinc lactate; zinc gluconate; zinc malate; zinc tartrate; zinc carbonate; zinc phosphate; and a mixture of two or more thereof;
    wherein said film comprises from about 0.1% to about 5%, by weight, of the oral care composition.

2. The composition of claim 1, wherein said film comprises about 50% of a zinc-containing compound.

3. The composition of claim 2, wherein said zinc-containing compound is zinc oxide or zinc citrate.

4. The composition of claim 3, wherein said zinc-containing compound is zinc oxide.

5. The composition of claim 1, wherein said film comprises from about 0.25% to about 3%, by weight, of the oral care composition.

6. The composition of claim 5, wherein said comprises from about 0.5% to about 2% by weight, of the oral care composition.

7. The composition of claim 1, wherein the zinc-containing compound comprises from about 0.5% to about 2.5%, by weight, of the oral care composition.

8. The composition of claim 7, wherein the zinc-containing compound comprises from about 1% to about 2%, by weight, of the oral care composition.

9. The composition of claim 1, wherein the film comprises a mixture of hydroxypropyl methylcelluloses, each having a different molecular weight.

10. The composition of claim 1, wherein the oral care composition is in the form of a dentifrice.

11. The composition of claim 1, wherein the film comprises less than 8% canola oil.

12. The composition of claim 1, wherein the film is substantially free of canola oil.

13. The film of claim 1, comprising about 40%-50% hydroxypropyl methyl cellulose, 40%-50% zinc oxide particles, 7.5%-9% propylene glycol and 1.25%-1.5% polysorbate 80.

* * * * *